(12) United States Patent
Bly

(10) Patent No.: US 8,311,647 B2
(45) Date of Patent: Nov. 13, 2012

(54) DIRECT DELIVERY SYSTEM FOR TRANSVASCULAR LEAD

(75) Inventor: Mark J. Bly, Falcon Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/079,512

(22) Filed: Apr. 4, 2011

(65) Prior Publication Data

US 2011/0178530 A1 Jul. 21, 2011

Related U.S. Application Data

(63) Continuation of application No. 11/669,047, filed on Jan. 30, 2007, now abandoned.

(51) Int. Cl.
*A61N 1/00* (2006.01)

(52) U.S. Cl. .......................... 607/127; 607/115; 607/131

(58) Field of Classification Search .................. 607/115, 607/127, 131
See application file for complete search history.

(56) References Cited

U.S. PATENT DOCUMENTS

| | | |
|---|---|---|
| 4,365,634 A | 12/1982 | Bare et al. |
| 4,414,986 A | 11/1983 | Dickhudt et al. |
| 4,774,949 A | 10/1988 | Fogarty |
| 4,905,667 A | 3/1990 | Foerster et al. |
| 4,920,979 A | 5/1990 | Bullara |
| 4,944,088 A | 7/1990 | Doan et al. |
| 5,016,808 A | 5/1991 | Heil, Jr. et al. |
| 5,170,802 A | 12/1992 | Mehra |
| 5,221,261 A | 6/1993 | Termin et al. |
| 5,265,608 A | 11/1993 | Lee et al. |
| 5,330,515 A | 7/1994 | Rutecki et al. |
| 5,351,394 A | 10/1994 | Weinberg |

(Continued)

FOREIGN PATENT DOCUMENTS

DE 10103288 8/2002

(Continued)

OTHER PUBLICATIONS

International Search Report and Written Opinion of international application No. PCT/US2008/051700, mailed Jun. 25, 2008, 13 pages.

(Continued)

*Primary Examiner* — Nicole F Lavert
(74) *Attorney, Agent, or Firm* — Faegre Baker Daniels LLP

(57) ABSTRACT

A lead delivery system for delivering a neurostimulation lead to a patient's internal jugular vein using a percutaneous stick. The system comprises a neurostimulation lead adapted to stimulate a vagus nerve from the internal jugular vein. The lead includes a proximal end, a distal end, a generally spiral shaped retaining structure interposed between the proximal and distal ends and configured to retain the lead in the internal jugular vein, an electrode coupled to the retaining structure, and a side port interposed between the retaining structure and the proximal end. The side port provides access to a lumen extending from the distal end to the side port. A guidewire is sized to fit within the side port and lumen and reduce a force exerted by the retaining structure against the internal jugular vein, thereby allowing rotation of the lead and orientation of the electrode by applying a torque to the lead. A catheter has a lumen sized to slideably receive the medical electrical lead and configured to provide access to the internal jugular vein from the percutaneous stick site. A method of delivering a medical electrical lead to a patient's internal jugular vein.

20 Claims, 8 Drawing Sheets

U.S. PATENT DOCUMENTS

| | | | |
|---|---|---|---|
| 5,354,318 | A | 10/1994 | Taepke |
| 5,378,239 | A | 1/1995 | Termin et al. |
| 5,383,922 | A | 1/1995 | Zipes et al. |
| 5,387,233 | A | 2/1995 | Alfemess et al. |
| 5,411,546 | A | 5/1995 | Sowald et al. |
| 5,423,865 | A | 6/1995 | Bowald et al. |
| 5,476,498 | A | 12/1995 | Ayers |
| 5,496,277 | A | 3/1996 | Termin et al. |
| 5,531,779 | A | 7/1996 | Dahl et al. |
| 5,540,730 | A | 7/1996 | Terry, Jr. et al. |
| 5,639,276 | A | 6/1997 | Weinstock et al. |
| 5,755,714 | A | 5/1998 | Murphy-Chutorian |
| 5,755,761 | A | 5/1998 | Obi no |
| 5,766,203 | A | 6/1998 | Imran et al. |
| 5,772,693 | A | 6/1998 | Brownlee |
| 5,792,187 | A | 8/1998 | Adams |
| 5,803,928 | A | 9/1998 | Tockman et al. |
| 5,871,531 | A | 2/1999 | Struble |
| 5,954,761 | A | 9/1999 | Machek et al. |
| 5,997,536 | A | 12/1999 | Osswald et al. |
| 6,006,134 | A | 12/1999 | Hill et al. |
| 6,021,354 | A | 2/2000 | Warman et al. |
| 6,055,456 | A | 4/2000 | Gerber |
| 6,292,695 | B1 | 9/2001 | Webster, Jr. et al. |
| 6,321,123 | B1 | 11/2001 | Morris et al. |
| 6,363,288 | B1 | 3/2002 | Bush et al. |
| 6,385,492 | B1 | 5/2002 | Ollivier et al. |
| 6,397,109 | B1 | 5/2002 | Cammilli et al. |
| 6,429,217 | B1 | 8/2002 | Puskas |
| 6,442,413 | B1 | 8/2002 | Silver |
| 6,449,507 | B1 | 9/2002 | Hill et al. |
| 6,516,232 | B2 | 2/2003 | Skinner |
| 6,522,926 | B1 | 2/2003 | Kieval et al. |
| 6,564,096 | B2 | 5/2003 | Mest |
| 6,584,362 | B1 | 6/2003 | Scheiner et al. |
| 6,600,956 | B2 | 7/2003 | Maschino et al. |
| 6,656,960 | B2 | 12/2003 | Puskas |
| 6,671,562 | B2 | 12/2003 | Osypka et al. |
| 6,704,604 | B2 | 3/2004 | Soukup et al. |
| 6,760,626 | B1 | 7/2004 | Boveja |
| 6,766,203 | B2 | 7/2004 | Doan et al. |
| 6,778,854 | B2 | 8/2004 | Puskas |
| RE38,654 | E | 11/2004 | Hill et al. |
| RE38,705 | E | 2/2005 | Hill et al. |
| 6,882,887 | B1 | 4/2005 | Shelchuk et al. |
| 6,889,092 | B2 | 5/2005 | Zhu et al. |
| 6,901,297 | B2 | 5/2005 | Frericks et al. |
| 6,934,583 | B2 | 8/2005 | Weinberg et al. |
| 6,934,589 | B2 | 8/2005 | Sundquist et al. |
| 6,973,340 | B2 | 12/2005 | Fuimaono et al. |
| 7,047,084 | B2 | 5/2006 | Erickson et al. |
| 7,058,454 | B1 | 6/2006 | Chitre et al. |
| 7,215,896 | B2 | 5/2007 | Yamada et al. |
| 7,676,275 | B1 | 3/2010 | Farazi et al. |
| 7,917,230 | B2 | 3/2011 | Bly |
| 7,949,409 | B2 | 5/2011 | Bly et al. |
| 2002/0026228 | A1 | 2/2002 | Schauerte |
| 2002/0029030 | A1 | 3/2002 | Lurie et al. |
| 2002/0032963 | A1 | 3/2002 | Lindegren |
| 2002/0087192 | A1 | 7/2002 | Barrett et al. |
| 2002/0151949 | A1 | 10/2002 | Dahl et al. |
| 2002/0183237 | A1 | 12/2002 | Puskas |
| 2002/0183817 | A1 | 12/2002 | Van Venrooij et al. |
| 2002/0198570 | A1 | 12/2002 | Puskas |
| 2002/0198571 | A1 | 12/2002 | Puskas |
| 2003/0074039 | A1 | 4/2003 | Puskas |
| 2003/0078623 | A1 | 4/2003 | Weinberg et al. |
| 2003/0105506 | A1 | 6/2003 | Krishnan et al. |
| 2003/0195506 | A1 | 10/2003 | Stewart et al. |
| 2003/0195603 | A1 | 10/2003 | Scheiner et al. |
| 2003/0199961 | A1 | 10/2003 | Bjorklund et al. |
| 2003/0229380 | A1 | 12/2003 | Adams et al. |
| 2004/0015151 | A1 | 1/2004 | Chambers |
| 2004/0015204 | A1 | 1/2004 | Whitehurst et al. |
| 2004/0015205 | A1 | 1/2004 | Whitehurst et al. |
| 2004/0019359 | A1 | 1/2004 | Worley et al. |
| 2004/0019377 | A1 | 1/2004 | Taylor et al. |
| 2004/0030362 | A1 | 2/2004 | Hill et al. |
| 2004/0059383 | A1 | 3/2004 | Puskas |
| 2004/0059404 | A1 | 3/2004 | Bjorklund et al. |
| 2004/0062852 | A1 | 4/2004 | Schroeder et al. |
| 2004/0133240 | A1 | 7/2004 | Adams et al. |
| 2004/0147825 | A1 | 7/2004 | Milojevic et al. |
| 2004/0172075 | A1 | 9/2004 | Shafer et al. |
| 2004/0172088 | A1 | 9/2004 | Knudson et al. |
| 2004/0172116 | A1* | 9/2004 | Seifert et al. ................... 607/119 |
| 2004/0176782 | A1 | 9/2004 | Hanse et al. |
| 2004/0186531 | A1 | 9/2004 | Jahns et al. |
| 2004/0260374 | A1* | 12/2004 | Zhang et al. ................... 607/122 |
| 2005/0021119 | A1* | 1/2005 | Sage et al. ...................... 607/122 |
| 2005/0038489 | A1 | 2/2005 | Grill |
| 2005/0060014 | A1 | 3/2005 | Swoyer et al. |
| 2005/0060015 | A1 | 3/2005 | Tanaka |
| 2005/0065553 | A1 | 3/2005 | Ben Ezra et al. |
| 2005/0080472 | A1 | 4/2005 | Atkinson et al. |
| 2005/0113862 | A1 | 5/2005 | Besselink et al. |
| 2005/0131467 | A1 | 6/2005 | Boveja |
| 2005/0143412 | A1 | 6/2005 | Puskas |
| 2005/0149126 | A1 | 7/2005 | Libbus |
| 2005/0149155 | A1 | 7/2005 | Scheiner et al. |
| 2005/0149156 | A1 | 7/2005 | Libbus et al. |
| 2005/0197675 | A1 | 9/2005 | David et al. |
| 2005/0251239 | A1 | 11/2005 | Wallace et al. |
| 2006/0206153 | A1 | 9/2006 | Libbus et al. |
| 2006/0229677 | A1 | 10/2006 | Moffitt et al. |
| 2006/0241737 | A1 | 10/2006 | Tockman et al. |
| 2006/0259085 | A1 | 11/2006 | Zhang et al. |
| 2006/0259107 | A1 | 11/2006 | Caparso et al. |
| 2006/0293741 | A1 | 12/2006 | Johnson et al. |
| 2007/0167955 | A1 | 7/2007 | De La Menardiere et al. |
| 2008/0051861 | A1 | 2/2008 | Cross et al. |
| 2008/0147168 | A1 | 6/2008 | Ransbury et al. |
| 2008/0167702 | A1 | 7/2008 | Ransbury et al. |
| 2008/0183186 | A1 | 7/2008 | Bly et al. |
| 2008/0183187 | A1 | 7/2008 | Bly |
| 2008/0183248 | A1 | 7/2008 | Rezai et al. |
| 2008/0183253 | A1 | 7/2008 | Bly |
| 2008/0183254 | A1 | 7/2008 | Bly et al. |
| 2008/0183255 | A1 | 7/2008 | Bly et al. |
| 2008/0183259 | A1 | 7/2008 | Bly et al. |
| 2008/0183264 | A1 | 7/2008 | Bly et al. |
| 2008/0183265 | A1 | 7/2008 | Bly et al. |
| 2009/0171425 | A1 | 7/2009 | Dahlberg |
| 2009/0276025 | A1 | 11/2009 | Burnes et al. |
| 2010/0023088 | A1 | 1/2010 | Stack et al. |
| 2010/0049289 | A1 | 2/2010 | Lund et al. |
| 2011/0152877 | A1 | 6/2011 | Bly |
| 2012/0035691 | A1 | 2/2012 | Tockman et al. |

FOREIGN PATENT DOCUMENTS

| | | |
|---|---|---|
| EP | 0453117 | 10/1991 |
| EP | 0795343 | 9/1997 |
| EP | 1208867 | 5/2002 |
| EP | 1304135 | 4/2003 |
| JP | 2005-049701 | 3/1993 |
| JP | 9187518 A | 7/1997 |
| WO | WO 8304181 | 12/1983 |
| WO | WO 9955412 | 11/1999 |
| WO | WO 9956817 | 11/1999 |
| WO | WO 0100273 | 1/2001 |
| WO | WO0137723 A2 | 5/2001 |
| WO | WO 0218006 | 3/2002 |
| WO | WO03084433 A2 | 10/2003 |
| WO | WO2005065771 A1 | 7/2005 |
| WO | WO 2006098996 | 9/2006 |
| WO | WO 2006110338 | 10/2006 |

OTHER PUBLICATIONS

International Search Report and Written Opinion of international application No. PCT/US2007/086130, mailed Apr. 9, 2008, 15 pages.

International Search Report and Written Opinion of international application No. PCT/US2007/086118, mailed May 21, 2008, 14 pages.

International Search Report and Written Opinion of international application No. PCT/US2007/086119, mailed Apr. 3, 2007, 15 pages.

International Search Report and Written Opinion of international application No. PCT/US2007/086120, mailed Apr. 14, 2008, 14 pages.

International Search Report and Written Opinion of international application No. PCT/US2007/086124, mailed Apr. 8, 2008, 14 pages.

International Search Report and Written Opinion of international application No. PCT/US2007/086125, mailed Apr. 9, 2008.

International Search Report and Written Opinion of international application No. PCT/US2007/086127, mailed Apr. 3, 2008, 15 pages.

Tarver et al., "Clinical Experience with a Helical Bipolar Stimulating Lead," PACE, October, Part 111992, pp. 1545-1556, vol. 15, Cyberonics. Inc., Webster, Texas and the Department of Neurosurgery, Baylor College of Medicine.

Li et al., "Vagal Nerve Stimulation Markedly Improves Long-Term Survival After Chronic Heart Failure in Rats," Circulation Journal of the American Heart Association, Dec. 8, 2003, pp. 120-124.

Nabutovsky et al., "Lead Design and Initial Applications of a New Lead for Long-Term Endovascular Vagal Stimulation," PACE, vol. 30, Jan. 2007 Supplement 1, pp. S215-S218.

Web Site, Guidant Fineline II Sterox and Fineline II Sterox EZ, http://www/guidant.com/productstemplates/cnn/ fineline _II_ sterox.shtml, Aug. 26, 2004, pp. 1-3.

Goldberger JJ, Kadish AH, Johnson D, Qi X. New Technique for Vagal Nerve Stimulation. J Neurosci Methods. Sep. 15, 1999; 91 (1-2): 109-14.

International Search Report issued in PCT/US2011/046635, mailed Oct. 26, 2011, 6 pages.

Thompson GW, Levet JM, Miller SM, Hill MR, Meffert WG, Kolata RJ, Clem MF, Murphy DA, Armour JA. Bradycardia Induced by Intravascular Versus Direct Stimulation of the Vagus Nerve. Ann Thorac Surg. Mar. 1998; 65 (3): 637-42.

\* cited by examiner

DIRECT DELIVERY SYSTEM FOR TRANSVASCULAR LEAD

CROSS-REFERENCE TO RELATED APPLICATIONS

This application is a continuation of U.S. application Ser. No. 11/669,047, filed Jan. 30, 2007, now abandoned, which is related to the following co-owned applications: application entitled DUAL SPIRAL LEAD CONFIGURATIONS, filed on Jan. 30, 2007, and assigned Ser. No. 11/668,887, now issued U.S. Pat. No. 7,949,409; ELECTRODE CONFIGURATIONS FOR TRANSVASCULAR NERVE STIMULATION, filed on Jan. 30, 2007, and assigned Ser. No. 11/668,957, published as publication no. US 2008/0183264, now abandoned; application entitled SPIRAL CONFIGURATIONS FOR INTRAVASCULAR LEAD STABILITY, filed on Jan. 30, 2007, and assigned Ser. No. 11/668,926, published as publication no. US 2008/0183259; METHOD AND APPARATUS FOR DELIVERING A TRANSVASCULAR LEAD, filed on Jan. 30, 2007, and assigned Ser. No. 11/669,042, published as publication no. US 2008/0183186, now abandoned; NEUROSTIMULATING LEAD HAVING A STENT-LIKE ANCHOR, filed on Jan. 30, 2007, and assigned Ser. No. 11/668,834, now issued U.S. Pat. No. 7,917,230; TRANSVASCULAR LEAD WITH PROXIMAL FORCE RELIEF, filed on Jan. 30, 2007, and assigned Ser. No. 11/669,039, published as publication no. US 2008/0183265, now abandoned; and SIDE PORT LEAD DELIVERY SYSTEM, filed on Jan. 30, 2007, and assigned Ser. No. 11/669,050, published as publication no. US 2008/0183255 now abandoned, all of which are herein incorporated by reference in their entirety for all purposes.

TECHNICAL FIELD

The present invention relates to medical electrical leads for nerve or muscle stimulation. The present invention more particularly relates to a system for direct delivery of a neurostimulation lead into an internal jugular vein and adjacent to a vagus nerve.

BACKGROUND

A significant amount of research has been directed both to the direct and indirect stimulation of nerves including the left and right vagus nerves, the sympathetic and parasympathetic nerves, the phrenic nerve, the sacral nerve, and the cavernous nerve to treat a wide variety of medical, psychiatric, and neurological disorders or conditions. More recently, stimulation of the vagus nerve has been proposed as a method for treating various heart conditions, including heart failure. Heart failure is a cardiac condition characterized by a deficiency in the ability of the heart to pump blood throughout the body and high filling pressure causing pulmonary fluid to build up in the lungs.

Typically, nerve stimulating electrodes are cuff- or impalement-type electrodes placed in direct contact with the nerve to be stimulated. These electrodes require surgical implantation and can cause irreversible nerve damage due to swelling or direct mechanical damage to the nerve. A less invasive approach is to stimulate the nerve through an adjacent vessel using an intravascular lead. A lead including one or more electrodes is inserted into a patient's vasculature and delivered to a site within a vessel adjacent a nerve to be stimulated.

Intravascular leads can be implanted using an over-the-wire technique where the lead includes a lumen extending the length of the lead and the lead is advanced over a guidewire to the desired location in the vein. Current over-the-wire leads, however, have lumens extending the length of the lead. This requires threading of the entire lead over the wire and results in a larger than desirable lead diameter. Furthermore, the lead generally travels an extensive distance through the vasculature, which requires navigability and flexibility of the lead. Thus, there is a need in the art for an intravascular medical electrical lead that can be implanted using an over-the-wire technique, yet does not require a lumen extending the length of the lead. There is also a need in the art for a lead that can be delivered directly to a desired location in the vasculature.

SUMMARY

In one embodiment, the invention is a lead delivery system for delivering a neurostimulation lead to a patient's internal jugular vein using a percutaneous stick. The system comprises a neurostimulation lead adapted to stimulate a vagus nerve from the internal jugular vein. The lead includes a proximal end, a distal end, a generally spiral shaped retaining structure interposed between the proximal and distal ends and configured to retain the lead in the internal jugular vein, an electrode coupled to the retaining structure, and a side port interposed between the retaining structure and the proximal end. The side port provides access to a lumen extending from the distal end to the side port. A guidewire is sized to fit within the side port and lumen and reduce a force exerted by the retaining structure against the internal jugular vein, thereby allowing rotation of the lead and orientation of the electrode by applying a torque to the lead. A catheter has a lumen sized to slideably receive the medical electrical lead and is configured to provide access to the internal jugular vein from the percutaneous stick site.

In another embodiment, the present invention is a lead delivery system for delivering a neurostimulation lead to a patient's internal jugular vein using a percutaneous stick. The system comprises a neurostimulation lead adapted to stimulate a vagus nerve from the internal jugular vein, the lead including a proximal end, a distal end, a retaining structure configured to retain the lead in the internal jugular vein interposed between the proximal and distal ends, and a side port interposed between the retaining structure and the proximal end. The side port provides access to a lumen extending from the distal end to the side port. A guidewire is sized to fit within the side port and lumen and reduce a force exerted by the retaining structure against a surface external to the retaining structure, thereby facilitating advancement and orientation of the lead. A catheter has a lumen sized to slideably receive the medical electrical lead and is configured to provide access to the internal jugular vein from the percutaneous stick site.

In another embodiment, the present invention is a method of directly delivering a neurostimulation lead to a patient's internal jugular vein. The method comprises inserting a catheter into the internal jugular vein using a percutaneous stick. A guidewire is inserted into a side port and through a lumen of a neurostimulation lead. The neurostimulation lead includes a proximal end, a distal end, a retaining structure interposed between the proximal and distal ends, and an electrode coupled to the retaining structure. The side port is interposed between the retaining structure and the proximal end and the lumen extends from the distal end to the side port. A portion of the neurostimulation lead is advanced through the catheter and the lead is oriented to a desired position in the internal jugular vein. The catheter and guidewire are removed.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
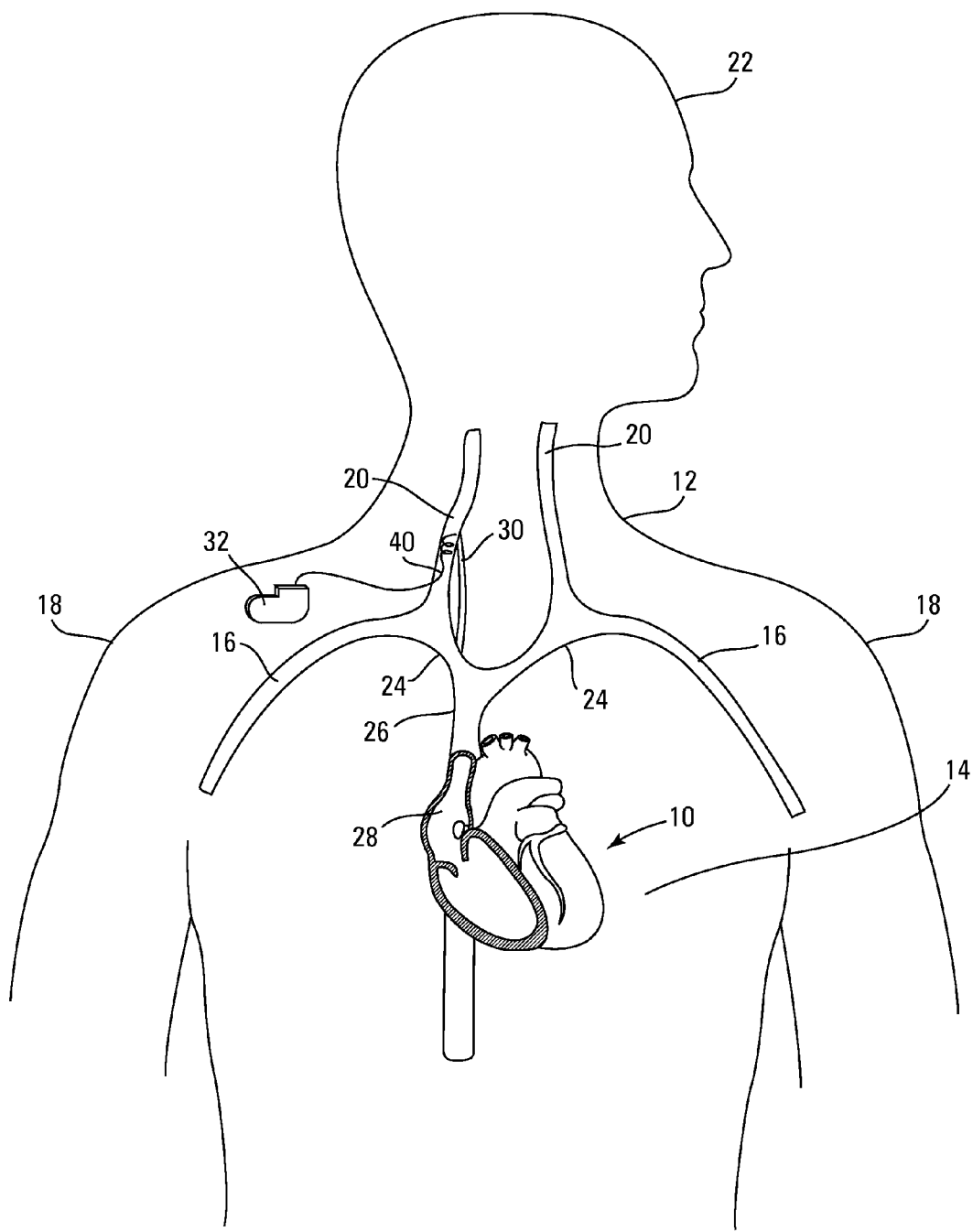
FIG. 1 is a schematic view of a patient's upper torso.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a schematic view of a patient's upper torso, including a heart 10 and the veins of the neck 12 and thorax 14. The subclavian veins 16 drain blood from the arms 18. The internal jugular veins 20 drain blood from the head 22 and join the subclavian veins 16 to form the brachiocephalic or innominate veins 24. The union of the brachiocephalic veins 24 forms the superior vena cava 26, which returns blood from the head 22, neck 12, arms 18, and thorax 14 to the right atrium 28. A vagus nerve 30 is shown adjacent to the right internal jugular vein 20. Another vagus nerve (not shown) is adjacent to the left internal jugular vein 20. A stimulating device 32 is located in a subcutaneous pocket near the patient's subclavian vein. The stimulating device 32 is connected to a medical electrical lead 40. A portion of the medical electrical lead 40 extends through the internal jugular vein 20 and the remainder is subcutaneously tunneled to the stimulating device 32. In one embodiment, the stimulating device 32 provides electrical stimulation to a nerve.

Figure 2:
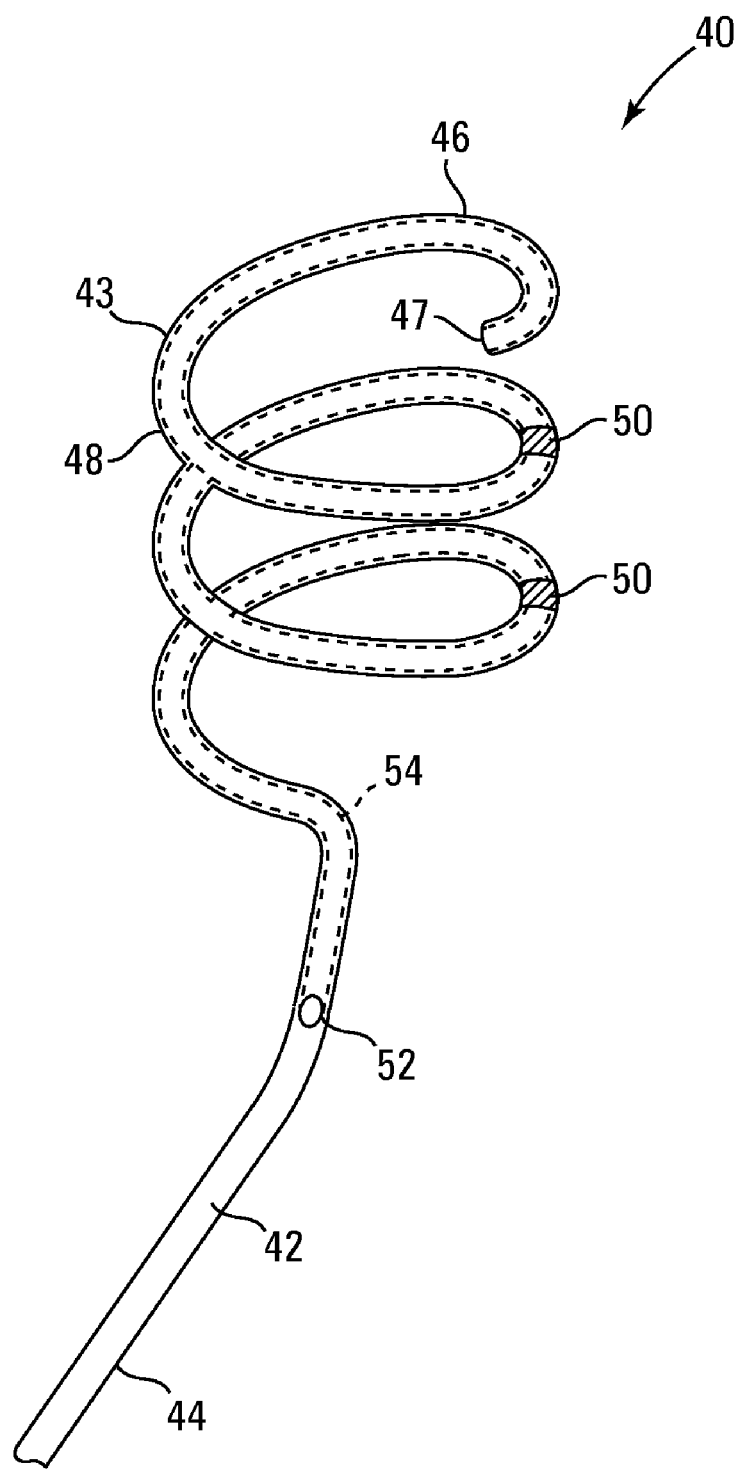
FIG. 2 is a schematic view of a medical electrical lead according to one embodiment of the present invention.

FIG. 2 is a schematic view of the medical electrical lead 40 of FIG. 1. The medical electrical lead 40 includes a lead body 42 comprised of an electrically insulative material 43 extending from a proximal end 44 to a distal end 46. The proximal end 44 is adapted for connection to the stimulating device 32 using connectors or any other means known in the art. A retaining structure 48 adapted to exert a force against a surface external to the retaining structure 48 is located at the distal end 46. In one embodiment, the retaining structure 48 exerts a force against the internal jugular vein 20. In another embodiment, the retaining structure 48 exerts a force against the catheter 60. In yet another embodiment, the retaining structure 48 exerts a force against both the catheter 60 and the internal jugular vein 20. The force exerted by the retaining structure 48 against the internal jugular vein 20 helps retain the electrodes 50 against the internal jugular vein 20 and adjacent to the vagus nerve 30. The retaining structure 48 also stabilizes the lead 40 within the internal jugular vein 20.

In the illustrated embodiment, the retaining structure 48 has a generally spiral shape. In one embodiment, the retaining structure 48 has a spiral shape as disclosed in pending published U.S. Patent Application US 2008/0183259, entitled SPIRAL CONFIGURATIONS FOR INTRAVASCULAR LEAD STABILITY, above-incorporated by reference in its entirety. In an alternative embodiment, the retaining structure 48 has the form of a dual spiral as disclosed in issued U.S. Pat. No. 7,949,409, entitled DUAL SPIRAL LEAD CONFIGURATIONS, above-incorporated by reference in its entirety. In another embodiment, the retaining structure 48 has the stent-like structure disclosed in issued U.S. Pat. No. 7,917,230, entitled NEUROSTIMULATING LEAD HAVING A STENT-LIKE ANCHOR, above-incorporated by reference in its entirety. In other embodiments, the retaining structure 48 has any shape that retains an electrode against a vessel.

The retaining structure 48 can be formed using molded silicone parts, metal conductor coils, heat formed polyurethane tubing, or any other method known in the art. The retaining structure 48 can have a variety of cross-sectional shapes, including circular or oval. In one embodiment, the retaining structure 48 is a spiral having a pitch of between approximately 0 and approximately 5 centimeters. In an alternative embodiment, the retaining structure 48 is a spiral having a diameter of between approximately 5 and approximately 50 millimeters. In another alternative embodiment, the retaining structure 48 has a length of between approximately 30 and approximately 200 millimeters.

Electrodes 50 are located at the distal end 46. In the embodiment shown in FIG. 2, the electrodes 50 are coupled to the retaining structure 48. The electrodes 50 can provide electrical stimulation, sense electrical activity, or both. The lead 40 includes conductive members (not shown) coupling electrodes 50 to the stimulating device 32. Although two electrodes 50 are shown in FIG. 2, the medical electrical lead 40 can include any number of electrodes 50. In the embodiment illustrated in FIG. 2, the electrodes 50 are ring electrodes. In other embodiments, the electrodes have any other configuration known in the art. In one embodiment, the electrodes 50 are configured according to commonly assigned published U.S. Patent Application US 2008/0183264, entitled ELECTRODE CONFIGURATIONS FOR TRANSVASCULAR NERVE STIMULATION, above-incorporated by reference in its entirety.

A side port 52 communicates with and provides access to a lumen 54 extending from the distal end 46 to the side port 52. As shown in FIG. 2, the lumen 54 extends out of the tip 47 of the medical electrical lead 40 and terminates at the side port 52. In another embodiment, the lumen 54 extends beyond the side port 52. In another embodiment, the lumen 54 extends substantially the length of the medical electrical lead 40. In yet another embodiment, the lumen 54 extends the length of the medical electrical lead 40. In one embodiment, the lumen 54 is separate from a lumen formed by a conductive coil member. In another embodiment, all or a portion of the lumen 54 is formed by a conductive coil member lumen. In yet another embodiment, the lumen 54 is formed from multiple serial lumens. The lumen 54 can extend through the lead body 42 or through silicone or polyurethane molded parts in the lead 40. In one embodiment, the electrodes 50 are ring electrodes having insulated lumens and the lumen 54 is at least partially formed from the insulated electrode lumens. In another embodiment, the electrodes 50 are only partially exposed and the lumen 54 passes through the electrodes 50.

The side port 52 is interposed between the retaining structure 48 and the proximal end 44. In one embodiment, the side port 52 is located a maximum of approximately 5 centimeters from the retaining structure 48. In one embodiment, the lead 40 has a length of between about 40 and about 100 centimeters and a diameter of between about 3 and about 8 French. In one embodiment, the lumen 54 has a diameter of between about 0.014 and about 0.042 inch.

Figure 3:
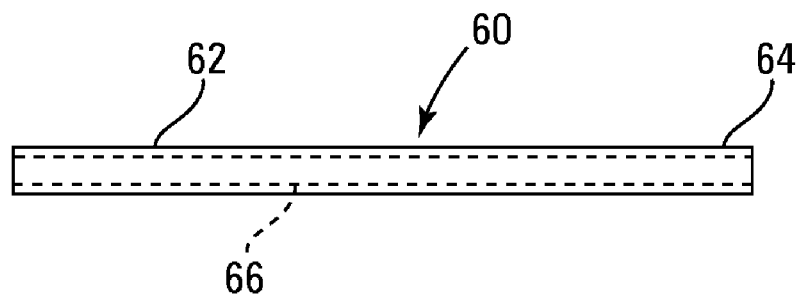
FIG. 3 is a schematic view of a catheter according to one embodiment of the present invention.
Figure 7:
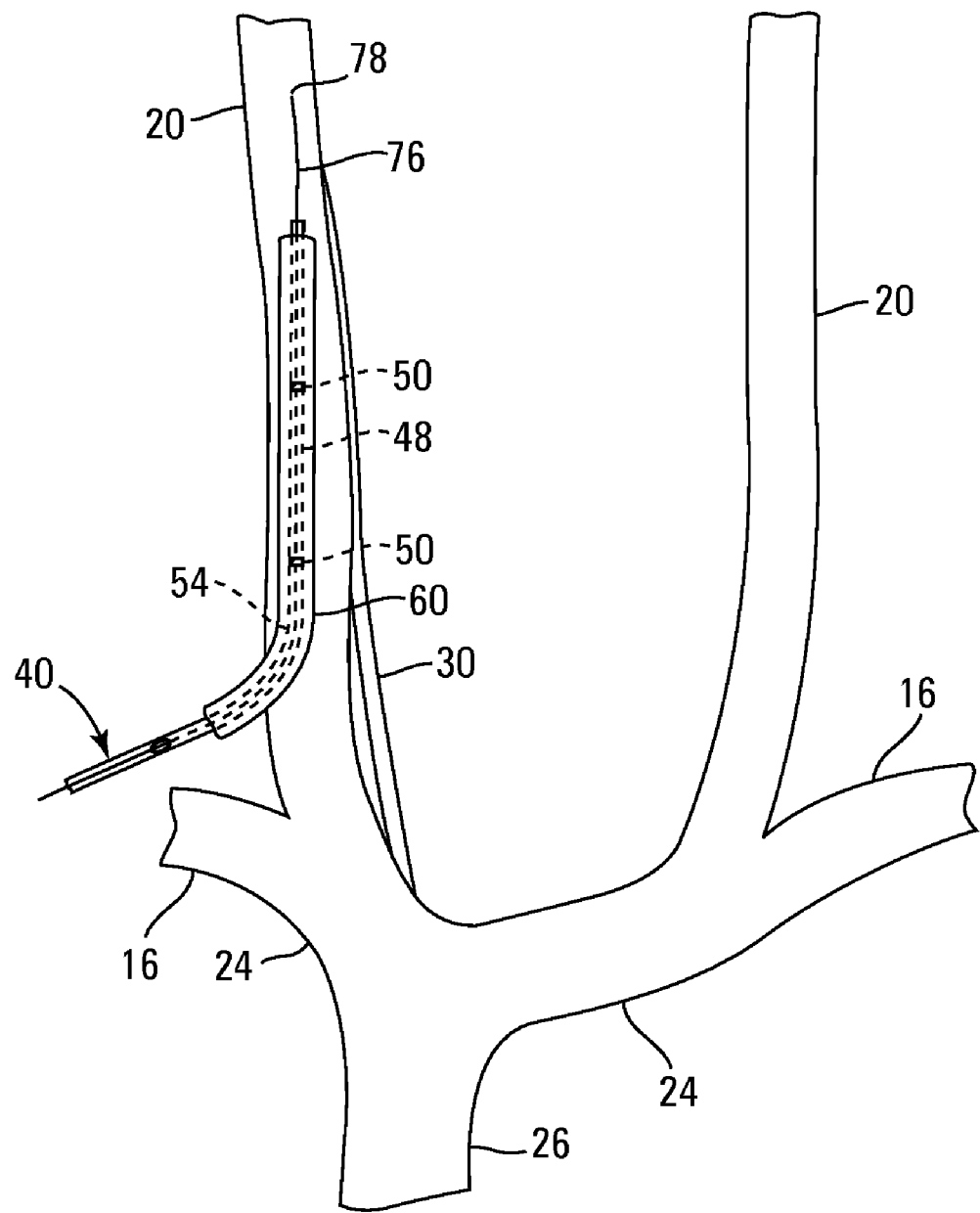
FIG. 7 is a schematic view of a medical electrical lead and guidewire inserted into a catheter according to one embodiment of the present invention.

FIG. 3 depicts an introducer or catheter 60 used to provide access to the internal jugular vein 20. The catheter 60 has a proximal end 62, a distal end 64, and a lumen 66. The catheter 60 is sized to slideably receive the medical electrical lead 40 in the lumen 66 after insertion of the guidewire 70 into the lead 40 (as shown in FIG. 7). In one embodiment, the catheter 60 is configured to provide access to the internal jugular vein 20 via percutaneous stick. The catheter 60 can be made of a polytetrafluoroethylene (PTFE) or fluorinated ethylene propylene (FEP) inner lining, a 304 V stainless steel braiding, and an outer jacket of Pebax and/or Nylon. Tungsten wire can optionally be added to the stainless steel braiding to improve radiopacity of the catheter. In other embodiments, the catheter 60 is made out of any other material known in the art. In one embodiment, the catheter 60 has a length of between about 10 and about 20 centimeters, an outer diameter of between about 6 and about 14 French, and an inner diameter that is slightly smaller than the outer diameter. In one embodiment, the inner diameter is about 0.020 inch smaller than the outer diameter.

Figure 4:
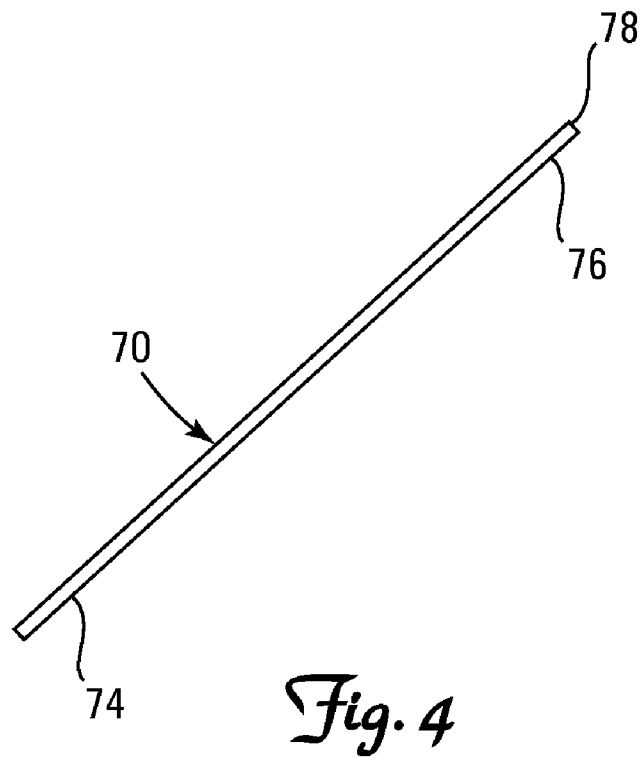
FIG. 4 is a schematic view of a guidewire according to one embodiment of the present invention.

FIG. 4 depicts a guidewire 70 according to one embodiment of the present invention. In the illustrated embodiment, the guidewire 70 has a proximal end 74, a distal end 76, and a distal tip 78. The guidewire 70 allows a clinician to introduce and position a medical electrical lead 40 in a patient. In one embodiment, the guidewire 70 has a core (not shown), and includes a coating, for example, a hydrophilic coating. In one embodiment, the wire core is made from nickel/titanium. In an alternative embodiment, the wire core is made from stainless steel. In yet another alternative embodiment, the wire core is made from any other metal known in the art. The guidewire 70 has an outer diameter that allows it to slide into the side port 52 and through the lumen 54 of the medical electrical lead 40. In one embodiment, the guidewire 70 has a diameter of between approximately 0.012 and approximately 0.040 inch. In one embodiment, the guidewire 70 includes a grind profile. In one embodiment, the grind profile is parabolic. In one embodiment, the guidewire 70 has a length of between about 10 and about 40 centimeters.

Figure 5:
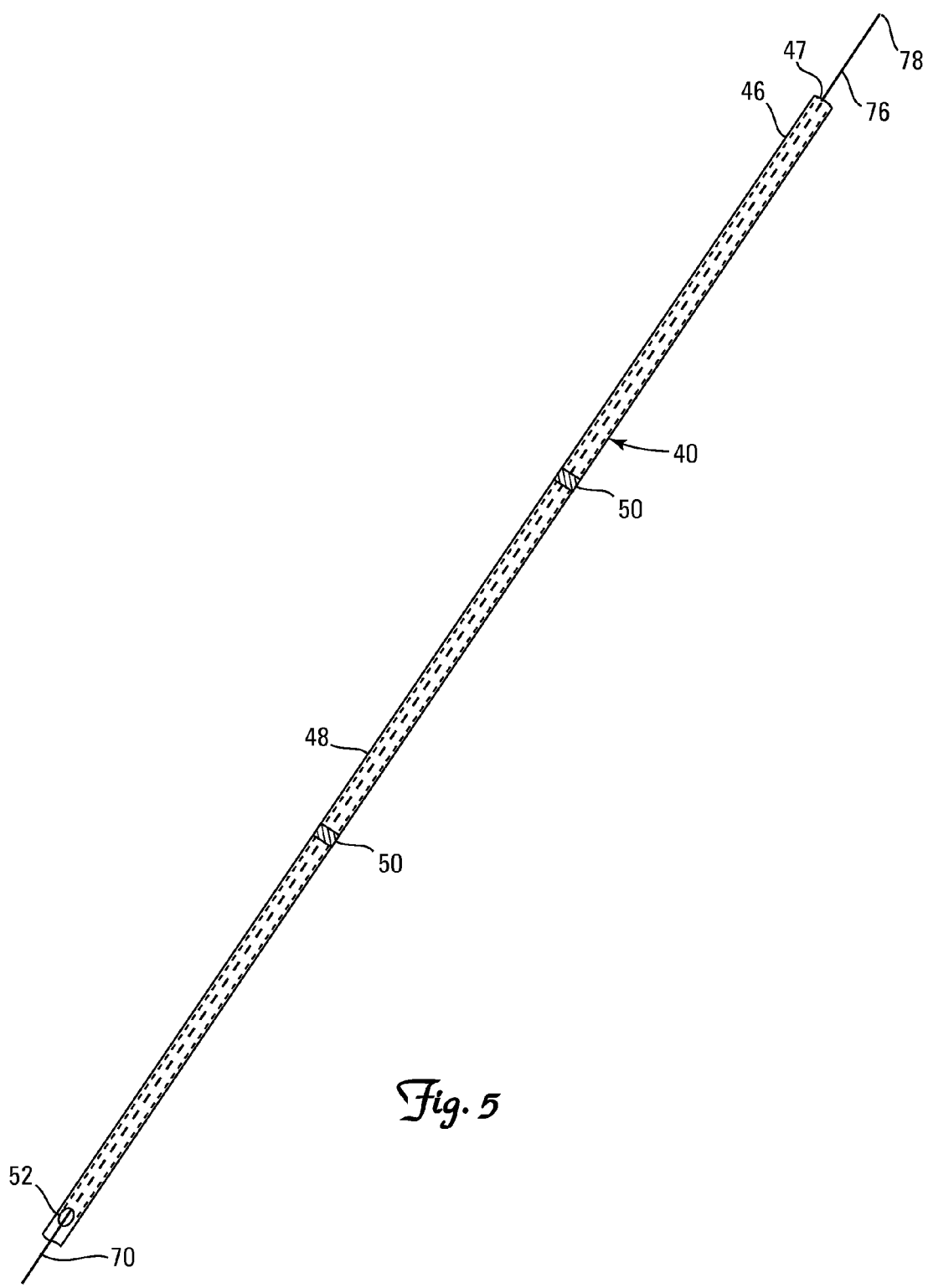
FIG. 5 is a schematic view of a guidewire inserted into a medical electrical lead according to one embodiment of the present invention.

FIG. 5 illustrates the medical electrical lead 40 after insertion of the guidewire 70 into the side port 52 and lumen 54. In one embodiment, the lead 40 is advanced over the guidewire 70 during implantation. In another embodiment, the guidewire 70 straightens the retaining structure 48 enough to reduce the force exerted on the internal jugular vein 20 by the retaining structure 48, thereby facilitating implantation of the lead 40. Although the medical electrical lead 40 is shown as straight after the insertion of the guidewire 70 in the illustrated embodiment, in another embodiment, the guidewire 70 does not completely straighten the retaining structure 48. The guidewire 70 is used to advance the medical electrical lead 40 through the catheter 60 and to a desired location in the internal jugular vein 20.

Figure 6:
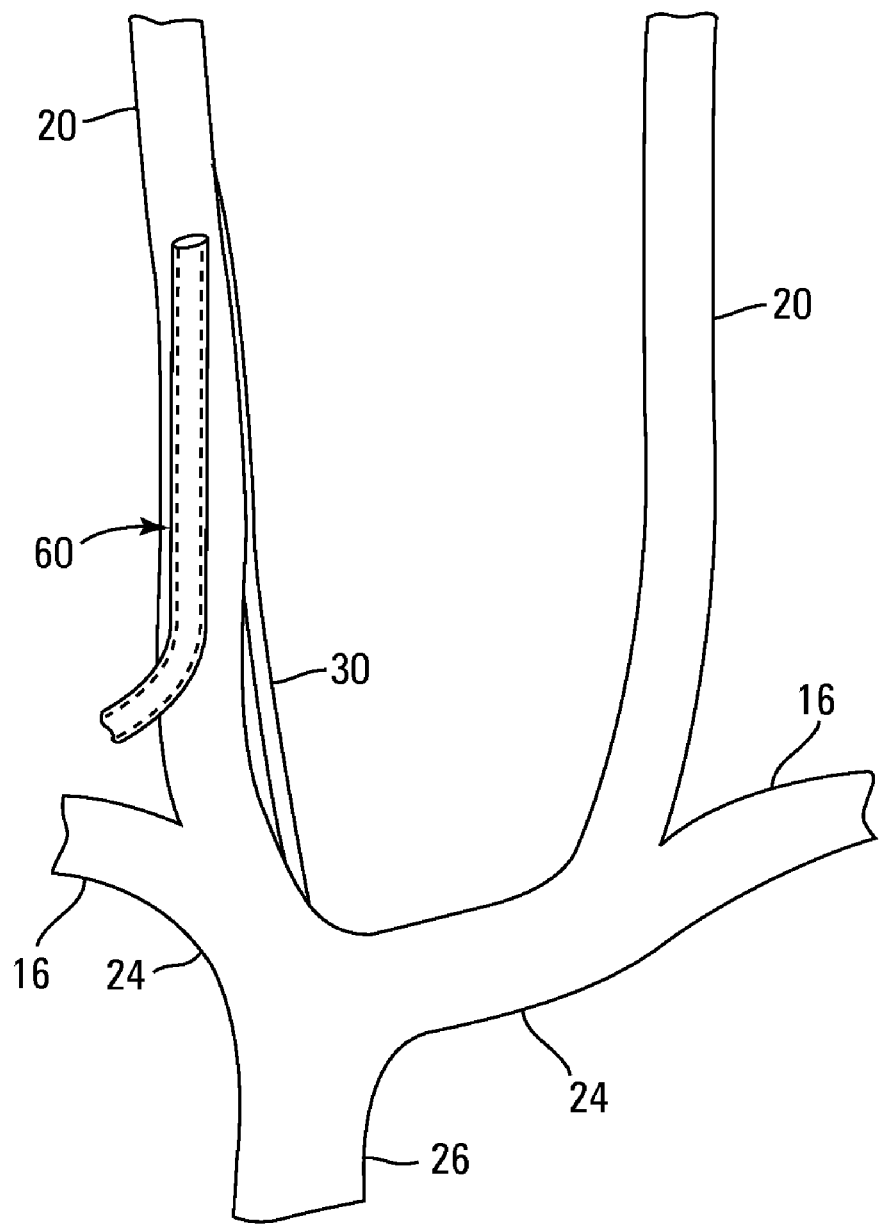
FIG. 6 is a schematic view of a catheter after insertion into an internal jugular vein according to one embodiment of the present invention.
Figure 8:
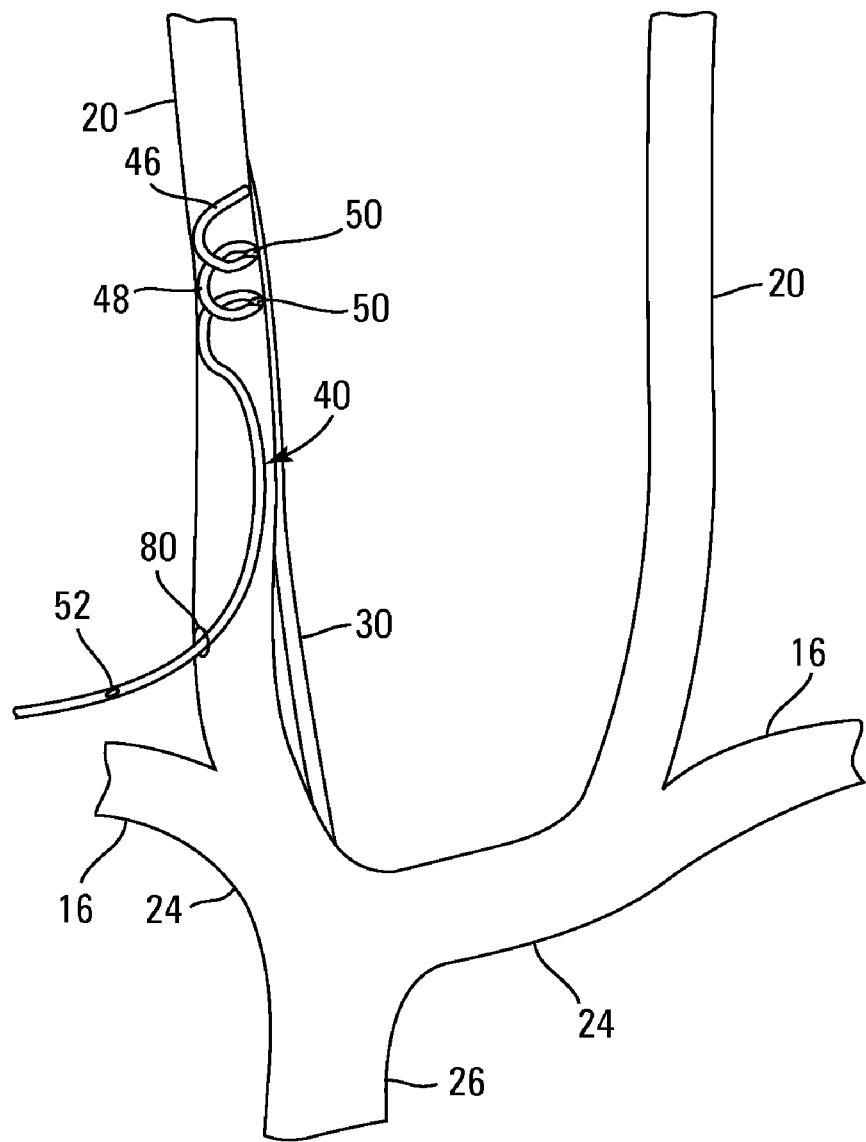
FIG. 8 is a schematic view of a medical electrical lead located in a patient's internal jugular vein after removal of the catheter and guidewire according to one embodiment of the present invention.

FIG. 6 is a schematic view showing the catheter 60 inserted into the internal jugular vein 20. The catheter 60 provides access to the internal jugular vein 20 for the lead 40. FIG. 7 is a cutaway view showing the medical electrical lead 40 and guidewire 70 after advancement through the catheter 60 and into the internal jugular vein 20. As shown in FIG. 8, after the catheter 60 and guidewire 70 are removed, the retaining structure 48 retains the distal end 46 of the lead 40 in the internal jugular vein 20. In one embodiment, the retaining structure 48 retains the electrodes 50 in a location adjacent to the vagus nerve 30. In one embodiment, the remainder of the medical electrical lead 40 is subcutaneously tunneled to the stimulating device 32.

In one embodiment, a suture 80 secures the distal end 46 of the medical electrical lead 40 at the site of the percutaneous stick. In another embodiment, a suture sleeve (not shown) can be used to protect the lead body 42 when using a suture 80 to secure the distal end 46. In yet another embodiment, an anchor or any other securing means known in the art is used to secure the proximal end 46 of the medical electrical lead 40.

Figure 9:
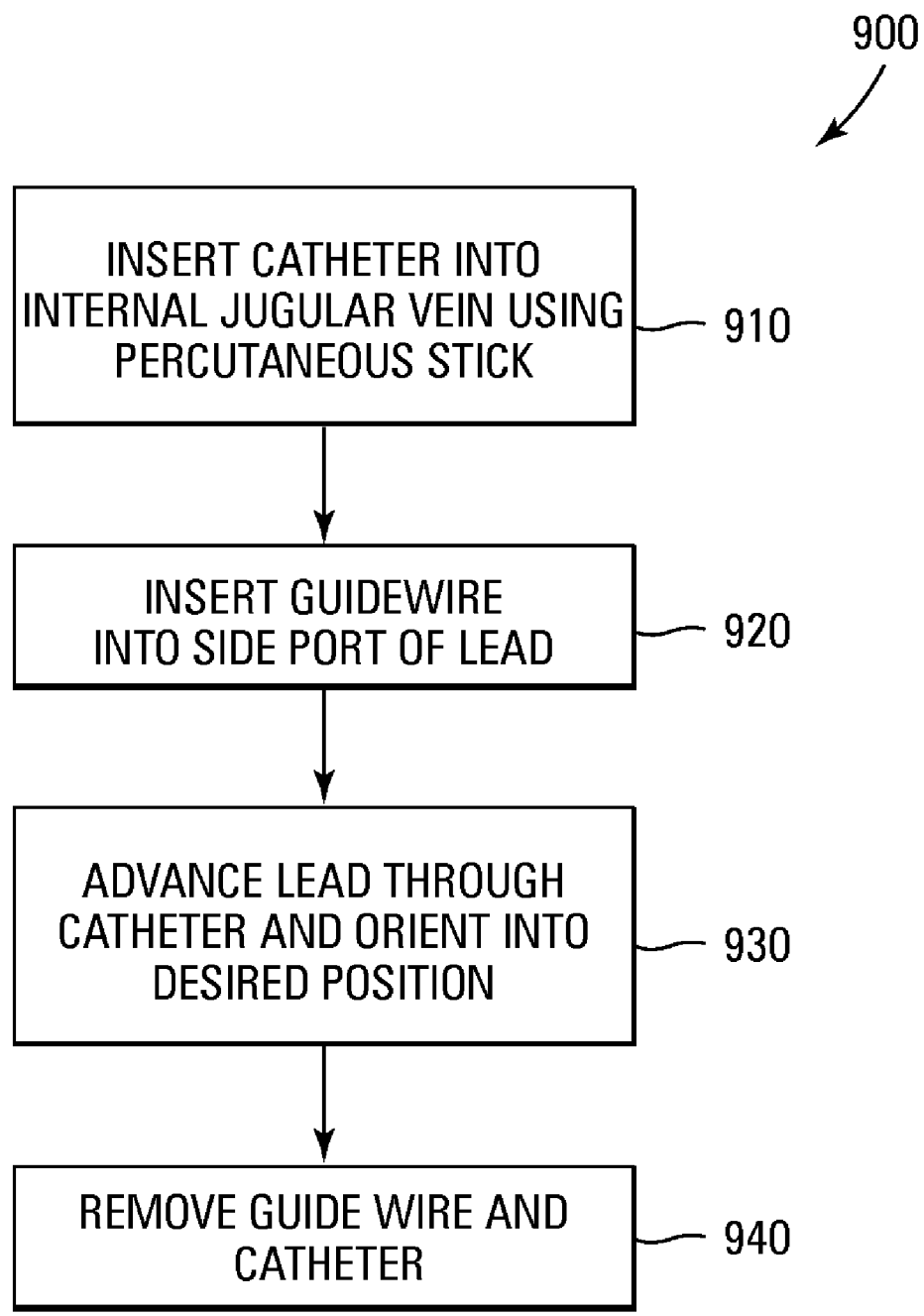
FIG. 9 is a flowchart illustrating an exemplary method of implanting a medical electrical lead into an internal jugular vein according to one embodiment of the present invention.

FIG. 9 depicts an exemplary method 900 for implanting a medical electrical lead 40. A catheter 60 is inserted into the internal jugular vein 20 using a percutaneous stick (block 910). A guidewire 70 (or stylet) is inserted into the side port 52 and through the lumen 54 of the medical electrical lead 40 (block 920). The lead 40 is advanced through the catheter 60 into the internal jugular vein 20 and oriented to a desired position (block 930). The guidewire 70 and catheter 60 are then removed (block 940). In one embodiment, the lead 40 is advanced over the guidewire 70 and through the catheter 60. In another embodiment, the lead 40 and the guidewire 70 are advanced through the catheter 60 together.

The lead 40 can be advanced and oriented to a desired position in a number of ways. For example, in one embodiment, a portion of the retaining structure 48 is retained in the catheter 60 and the retaining structure 48 exerts a force against the catheter 60. The lead 40 can be oriented by applying a torque to the catheter 40 or to the lead body 42. In another embodiment, the entire retaining structure 48 is retained in the catheter 60 and the lead 40 is oriented by applying a torque to the catheter 40 or to the lead body 42. In yet another embodiment, a guidewire 70 inserted into the side port 52 and lumen 54 of the lead 40 straightens the retaining structure 48 to reduce the force exerted by the retaining structure 48 on the catheter 60. This force reduction facilitates advancement of the lead 40 through the catheter 60 and the internal jugular vein 20. The force reduction also facilitates orientation of the lead 40 in the internal jugular vein 20. In one embodiment, the lead 40 is advanced and oriented so that the electrodes 50 are adjacent to the vagus nerve 30.

In another embodiment, the retaining structure 48 extends beyond the distal end 64 of the catheter. The lead 40 is oriented by applying a torque to the lead body 42. In one embodiment, the guidewire 70 is used to reduce the force exerted by the retaining structure 48 on the internal jugular vein 20 during implantation of the lead 40. In another embodiment, the guidewire 70 is retracted from the retaining structure 48, yet remains in a portion of the lumen 54, thereby allowing for additional manipulation of the lead 40 using the guidewire 70.

In one embodiment, removal of the catheter 60 allows the retaining structure 48 to further expand, causing the retaining structure 48 to exert a greater force against the internal jugular vein 20. In one embodiment, the catheter 60 is split or peeled apart for removal. In another embodiment, the catheter 60 is slid over the medical electrical lead 40. In one embodiment, a stylet is inserted into the lumen 54 instead of a guidewire 70. In another embodiment, the lumen 54 does not extend out of the tip 47 of the medical electrical lead 40 and a stylet (not shown) is used to push the lead 40 to the desired position in the internal jugular vein 20. In yet another embodiment, the method 900 includes securing the distal end 46 of the lead 40 at the stick site using a suture 80. In another embodiment, the remainder of the lead 40 is subcutaneously tunneled to a stimulating device 32.

The invention allows for direct delivery of the medical electrical lead 40 into the internal jugular vein 20 without threading the guidewire 70 through the entire length of the lead 40. It is easier to exchange guidewires 70, if necessary, because the guidewire 70 is not threaded through the entire length of the lead 40. Additionally, the lead 40 is more easily turned because instead of turning the entire length of the lead 40, a shorter length may be turned. In one embodiment, the lead 40 is turned by applying a torque to the lead body 42 at a region near the side port 52.

Although the present invention has been described in reference to an internal jugular vein, the invention could also be used to implant a lead 40 in any vessel, such as a vein, artery, lymphatic duct, bile duct, for the purposes of nerve or muscle stimulation. The medical electrical lead 40 can include any number of conductors, electrodes, terminal connectors, and insulators, and can be used with any combination of catheters, introducers, guidewires, and stylets.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A method of directly delivering a neurostimulation lead to a patient's internal jugular vein, the method comprising:
    inserting an introducer into the internal jugular vein using a percutaneous stick;
    inserting a guidewire into and through a lumen of a neurostimulation lead, the neurostimulation lead including a proximal end, a distal end, a retaining structure interposed between the proximal and distal ends, and an electrode coupled to the retaining structure;
    advancing a portion of the neurostimulation lead through the introducer and orienting the lead to a desired position in the internal jugular vein; and
    removing the introducer and the guidewire.

2. The method of claim 1 wherein the neurostimulation lead includes a side port interposed between the retaining structure and the proximal end, the lumen extends from the distal end to the side port, and wherein inserting the guidewire into and through the lumen of the neurostimulation lead comprises inserting the guidewire into the side port.

3. The method of claim 2 wherein a distance between the side port and the retaining structure is a maximum of about 5 centimeters.

4. The method of claim 1 wherein advancing a portion of the neurostimulation lead comprises advancing the retaining structure beyond a distal end of the introducer and orienting the lead comprises turning the lead.

5. The method of claim 1 further comprising reducing a force exerted by the retaining structure against a surface external to the retaining structure by inserting the guidewire through the lumen.

6. The method of claim 1 wherein orienting the lead comprises orienting the electrode so the electrode is adjacent to a vagus nerve.

7. The method of claim 1 wherein the retaining structure comprises a generally spiral shaped retaining structure.

8. The method of claim 7 wherein the generally spiral shaped retaining structure has a diameter of between about 5 millimeters and about 50 millimeters.

9. The method of claim 7 wherein the generally spiral shaped retaining structure has a pitch of between about 0 centimeters and about 5 centimeters.

10. A method of directly delivering a neurostimulation lead to a patient's internal jugular vein, the method comprising:
    inserting an introducer into the internal jugular vein;
    inserting a stylet into and through a lumen of a neurostimulation lead, the neurostimulation lead including a proximal end, a distal end, a retaining structure interposed between the proximal and distal ends, and an electrode coupled to the retaining structure;
    advancing a portion of the neurostimulation lead through the introducer and orienting the lead to a desired position in the internal jugular vein; and
    removing the introducer and the stylet.

11. The method of claim 10 wherein inserting a stylet into and through a lumen of the neurostimulation lead comprises inserting the stylet into a side port disposed within the neurostimulation lead.

12. The method of claim 10 wherein advancing a portion of the neurostimulation lead comprises advancing the retaining structure beyond a distal end of the introducer and orienting the lead comprises turning the lead.

13. The method of claim 10 further comprising reducing a force exerted by the retaining structure against a surface external to the retaining structure by inserting the stylet through the lumen.

14. The method of claim 10 wherein orienting the lead comprises orienting the electrode so the electrode is adjacent to a vagus nerve.

15. The method of claim 10 wherein the neurostimulation lead has a diameter of between about 3 and about 8 French.

16. The method of claim 10 wherein the introducer has a length of between about 10 and about 20 centimeters.

17. A method of directly delivering a neurostimulation lead to a patient's internal jugular vein, the method comprising:
    inserting an introducer into the internal jugular vein;
    inserting a straightening member into a lumen of a neurostimulation lead, the neurostimulation lead including a proximal end, a distal end, a retaining structure interposed between the proximal and distal ends, and an electrode coupled to the retaining structure;
    advancing a portion of the neurostimulation lead through the introducer and orienting the lead to a desired position in the internal jugular vein; and
    removing the introducer and the straightening member.

18. The method of claim 17 wherein inserting a straightening member into a lumen of the neurostimulation lead comprises inserting the straightening member into a side port of the neurostimulation lead.

19. The method of claim 17 wherein advancing a portion of the neurostimulation lead comprises advancing the retaining structure beyond a distal end of the introducer and orienting the lead comprises turning the lead.

20. The method of claim 17 wherein orienting the lead comprises orienting the electrode so the electrode is adjacent to a vagus nerve.

* * * * *